United States Patent
Lacombe et al.

(10) Patent No.: US 7,438,415 B2
(45) Date of Patent: Oct. 21, 2008

(54) EYE EXAMINATION DEVICE BY MEANS OF TOMOGRAPHY WITH A SIGHTING DEVICE

(75) Inventors: François Lacombe, Chaville (FR); David Lafaille, Meudon (FR); Marie Glanc, Meudon (FR); Eric Gendron, Meudon (FR); Douchane Stefanovitch, Meudon (FR)

(73) Assignees: Centre National de la Recherche Scientifique, Paris (FR); Observatoire de Paris, Paris (FR); Mauna Kea Technologies, Paris (FR)

( * ) Notice: Subject to any disclaimer, the term of this patent is extended or adjusted under 35 U.S.C. 154(b) by 0 days.

(21) Appl. No.: 10/586,839

(22) PCT Filed: Jan. 21, 2005

(86) PCT No.: PCT/FR2005/000133

§ 371 (c)(1),
(2), (4) Date: Jul. 20, 2006

(87) PCT Pub. No.: WO2005/079655

PCT Pub. Date: Sep. 1, 2005

(65) Prior Publication Data

US 2007/0177104 A1 Aug. 2, 2007

(30) Foreign Application Priority Data

Jan. 22, 2004 (FR) .................................. 04 00581

(51) Int. Cl.
*A61B 3/10* (2006.01)
*A61B 3/14* (2006.01)
*A61B 3/00* (2006.01)

(52) U.S. Cl. ........................ 351/211; 351/209; 351/200

(58) Field of Classification Search ......... 351/200–211, 351/237, 246, 243
See application file for complete search history.

(56) References Cited

U.S. PATENT DOCUMENTS

| 3,836,238 | A | | 9/1974 | Munnerlyn et al. ......... 351/243 |
|---|---|---|---|---|
| 5,565,949 | A | | 10/1996 | Kasha, Jr. .................... 351/224 |
| 5,777,719 | A | * | 7/1998 | Williams et al. ............ 351/212 |
| 6,271,914 | B1 | * | 8/2001 | Frey et al. .................... 356/124 |
| 6,588,900 | B1 | * | 7/2003 | Le Gargasson et al. ..... 351/200 |
| 7,006,232 | B2 | * | 2/2006 | Rollins et al. ................ 356/479 |

FOREIGN PATENT DOCUMENTS

| WO | WO 03/020121 A1 | 3/2003 |
|---|---|---|
| WO | WO 03/105678 A2 | 12/2003 |

* cited by examiner

*Primary Examiner*—Mohammed Hasan
(74) *Attorney, Agent, or Firm*—Greer, Burns & Crain, Ltd.

(57) ABSTRACT

A sighting device is provided for an examination of the eye, including at least one moving target with a programmable form and trajectory, the target being displayed on a visualisation unit, such as an appropriate screen and visible from both eyes during the examination. An in-vivo tomographical eye examination system is also provided, including: a Michelson interferometer, generating a full-field OCT image, adaptable optical apparatus, arranged between the interferometer and an eye for examination, achieving the correction of the wavefronts coming from the eye and also the wavefronts going to the eye, detection apparatus, arranged after the interferometer, permitting the interferometric measurement by the OCT principle without modulation nor synchronized detection and a sighting device, with at least one mobile target with a programmable form and trajectory, the target being displayed on an appropriate screen and visible from at least one of the eyes during the examination.

5 Claims, 3 Drawing Sheets

EYE EXAMINATION DEVICE BY MEANS OF TOMOGRAPHY WITH A SIGHTING DEVICE

BACKGROUND

This invention relates to a sighting device for an examination of the eye. It also relates to a sighting method implemented in this device, as well as a system for examining the eye by in vivo tomography equipped with this device.

While examining the eye in general and the retina in particular, unconscious movements of the eye, even during a fixation, can considerably limit the performance of the examination.

Residual movements during a fixation are of three types:

Physiological nystagmus (or tremor): very rapid oscillations (from 40 to 100 Hz), of low amplitude (movement of images of the order of a micron on the retina);

Drift: slow movements (1 µm in a few ms), decorrelated from one eye to the other;

Micro-saccades: very rapid movements (a few hundreds per second), correlated between the eyes, for approximate recentring of the field.

Experience shows that fixation performances for a given subject are very variable, depending on the subject's state of fatigue, the ambient lighting or the fixation period. It is also known that fixation with both eyes is better than with a single eye.

The addition of a system for compensating movements of the eye may be shown to be very complex, costly, and sometimes incompatible with the existing instrumentation.

SUMMARY

The purpose of this invention is to remedy these drawbacks, by proposing a sighting device which optimises the subject's fixation performance, this sighting device being intended to equip an examination system by procuring for it a very good spatial resolution. This therefore improves the overall performance of the examination by improving that of the subject.

According to the invention, the sighting device comprises at least one moving target having a programmable shape and trajectory, this or these target(s) being displayed on viewing means such as a screen and visible by both eyes during the examination period.

In a first operating mode, the target(s) is/are moved so as to alternate fixation intervals on a given position with intervals termed rest on one or more other positions. The duration of the fixation intervals may be adjusted in order to optimise the quality. The diversity, position and duration of the rest positions may also be adjusted.

In a second operating mode, a continuous movement is ordered, which forces the subject to concentrate on a moving target. If the tracking performances are better than those of fixation, a priori knowledge of the trajectory enables readjustment of the images of the eye obtained with more accuracy than if the subject is observing a stationary target.

According to another aspect of the invention, a system for examining the eye by in vivo tomography is proposed, comprising:

a Michelson interferometer, producing a full field OCT setup, an adaptive optical device, arranged between the interferometer and an eye to be examined, producing correction of the wavefronts originating from the eye as well as those reaching the eye, and a detection device, arranged downstream of the interferometer, capable without synchronous modulation or detection, of carrying out the interferometric measurement according to the OCT principle, characterized in that it also comprises a sighting device according to the invention, comprising at least one moving target, having a programmable shape and trajectory, said target being displayed on viewing means and visible from at least one of the two eyes of said patient throughout the examination.

This sighting device enables to guide the sight of the patient while at the same time ensuring his visual comfort and optimizing his fixation performances.

Other advantages and characteristics of the invention will become apparent on examination of the detailed description of an embodiment which is in no way limitative, and the attached diagrams, in which:

DETAILED DESCRIPTION

Figure 1:
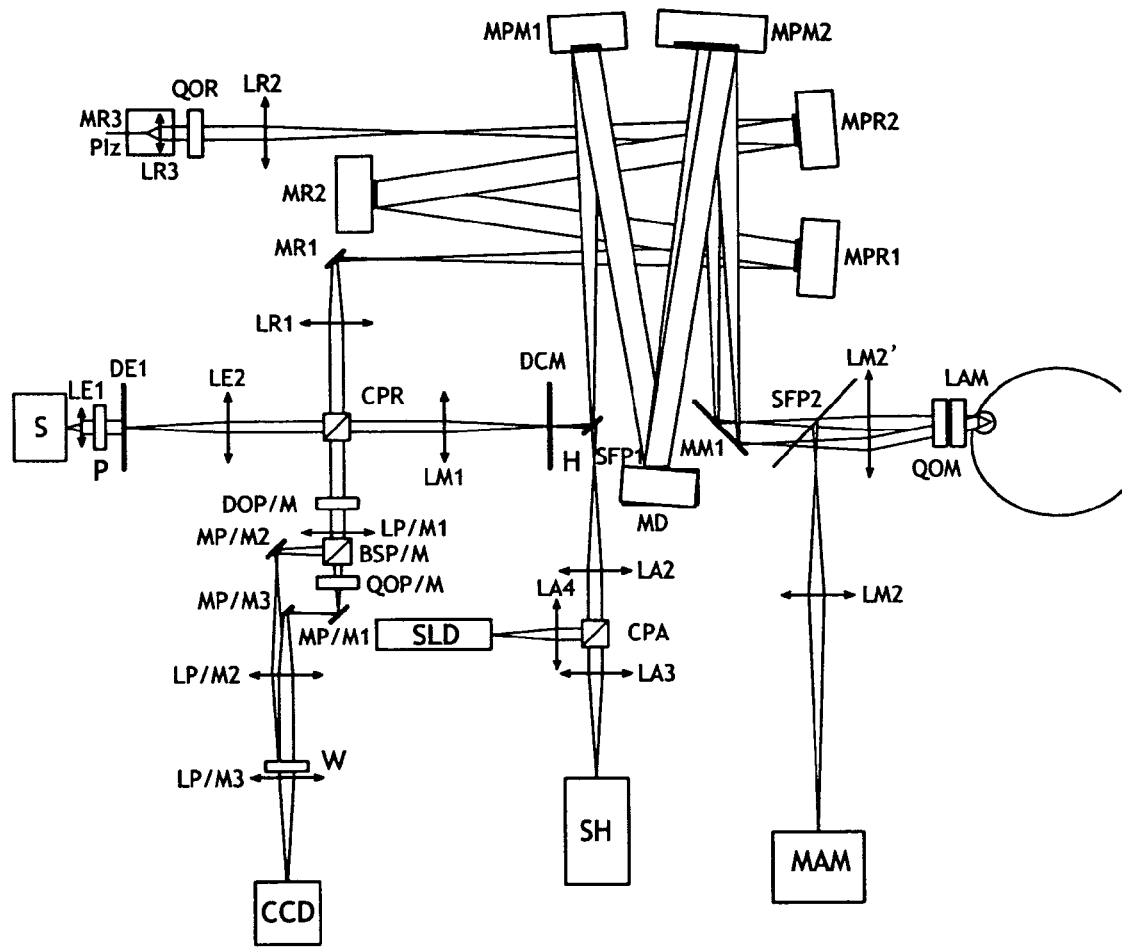
FIG. 1 illustrates the structure of an in vivo tomography system incorporating a sighting device according to the invention.

We will now describe, with reference to FIG. 1, a practical embodiment of an in vivo tomography system according to the invention. This system comprises an interferometer of the Michelson type, comprising a measurement arm designed to illuminate the eye and collect the returned light and a reference arm designed to illuminate a moving mirror enabling in depth exploration of the retinal tissue.

The interferometer is used with light polarized rectilinearly and perpendicularly in the two arms. The light source S is a diode with a short temporal coherence length (for example, 12 µm), the spectrum of which is centred on 780 nm. In theory, it confers on the in vivo tomography an axial resolution equal to half the coherence length divided by the refractive index of the medium.

This light source S may be pulsed. In this case, it is then synchronised with the shot of the image and the adaptive correction. The beam is limited by a field diaphragm corresponding to 1 degree in the field of view of the eye (300 µm on the retina) and a pupil diaphragm corresponding to an opening of 7 mm on a dilated eye.

An input polarizer P enables optimal balancing of the flux injected into the two arms of the interferometer.

The two arms have a configuration termed Gauss, afocal, which enables the conjugation of the pupils on the one hand, and the materialisation of an intermediate image of the field where a diaphragm blocks a large part of the corneal reflection, on the other hand. Quarter-wave plates ensure by the rotation of polarization of the sole light returned by the eye, and the moving mirror, an effective filtering of parasitic reflections in the in vivo tomography system according to the invention.

In order to maintain the equality of the optical paths in the two arms, with the same conjugation of the pupils and the field, the reference arm is similar to the measurement arm but with a static optic.

The detection path of the in vivo tomography system according to the invention will now be described. The two beams on the output arm are still polarized perpendicularly, and they interfere only if they are projected on a common direction. A Wollaston W prism has the function of simultaneously projecting the two radiations on two perpendicular analysis directions. A simultaneous measurement of the intensity may then be made after interference in two interference states in opposition, without synchronous modulation or detection, on a single two-dimensional detector. The addition of a quarter-wave plate, after division of the beam, makes it possible to access two additional measurements, thus removing any ambiguity between the amplitude and phase of the fringes. A half-wave plate at the input to the detection path enables suitable orientation of the incident polarizations.

The Wollaston prism is placed in a pupil plane, hence conjugated with the separator cube of the Michelson interferometer. The separation angle of the Wollaston prism is chosen as a function of the field to be observed. The focal length of the final objective determines the sampling interval of the four images.

The detector is of the CCD type, with an image rate of more than 30 images per second. This detector is associated with a dedicated computer (not shown) in which the digital processing of the images is carried out: extraction of the four measurements, calibration, calculation of the amplitude of the fringes.

The adaptive correction of the wavefronts is carried out upstream of the interferometer and thus in the measurement arm. Each point of the source S thus sees its image on the retina corrected of aberrations, and the return image is also corrected. The amplitude of the fringes is thus maximum.

The adaptive optics sub-assembly comprises a deformable mirror MD. Measurement of the wavefront is carried out by an analyser SH of the Shack-Hartmann type on the return beam of a luminous spot itself imaged on the retina via the deformable mirror MD. The analysis wavelength is 820 nm. Illumination is continuous and provided by a temporally incoherent superluminescent diode SLD. The dimensioning of the analyser corresponds to an optimisation between photometric sensitivity and wavefront sampling. The control refreshment frequency of the deformable mirror MD may reach 150 Hz. A dedicated computer (not shown) manages the adaptive optical loop. The control is, however, synchronised in order to freeze the shape of the mirror during the interferometer measurement.

An appropriate control on the focussing of the analysis path, using a lens LA2, enables to adapt the focussing distance to the layer selected by the interferometer. This arrangement is essential for maintaining an optimum contrast at any depth.

The deformable mirror MD is conjugated with the pupil of the system and of the eye. The field of the system is defined by the system input field diaphragm DCM. It should preferably be chosen to be a value less than that of the isoplanetism field of the eye, which guarantees the validity of the adaptive correction in the field of the only wave front measurement made from the spot, at the centre of the field. For example, the system field may be chosen equal to 1 degree, but the value of this field could be increased.

Moreover, the rotation of the deformable mirror MD makes it possible to choose the angle of arrival of the beam in the eye and thus the portion of the retina studied.

The addition of corrective lenses to the subject's view, thus low orders of geometric aberrations such as focus or astigmatism, just in front of the eye, makes it possible to loosen the requirements on the travel of the deformable mirror MD, and also guarantee an improved sighting. An adaptive corrective system by transmission may be used in preference to fixed lenses for an optimum correction.

Figure 3:
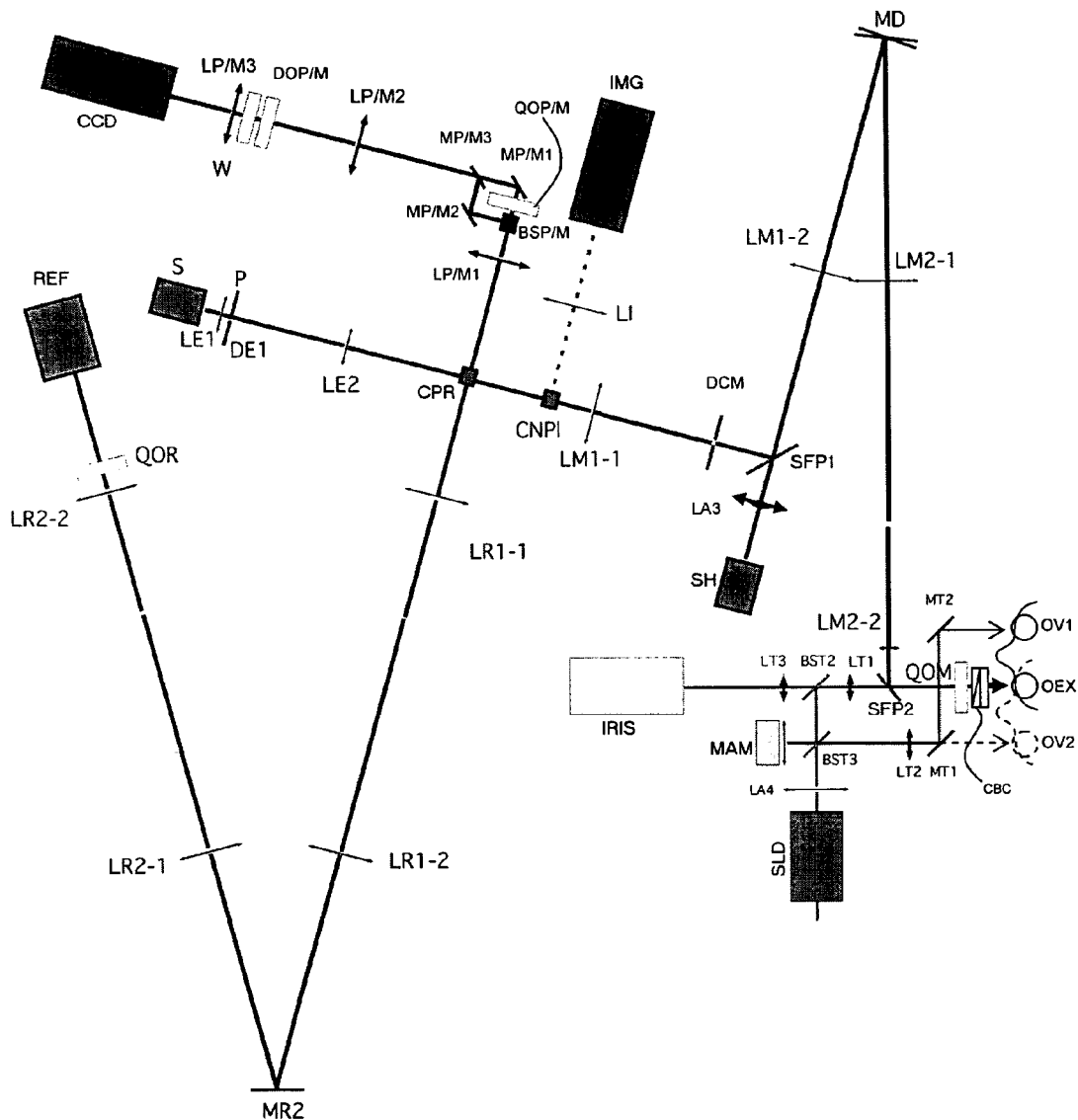
FIG. 3 is a diagram of another example of an embodiment of an in vivo tomography system according to the invention.

As illustrated in FIG. 3, the system may also comprise conventional imaging means, such as a camera IMG, capable of combining interferometric measurements with a simple imaging of the zones examined, for example to facilitate the exploration and selection of the zones to be examined.

Arranged directly at the output (the return) of the measurement arm, and therefore just before of the polarizing cube CPR of the interferometer, a second polarizing cube CNPI may deflect the return beam towards an imaging camera IMG having its own means LI of focussing the image. On this path, a direct image of the sighted retinal zone will be observable. In particular the measurement arm and this additional path may be arranged such that they provide a wider field of observation than the interferometric mode, the field of which is limited, in particular by the interferometric contrast measurement technique in itself.

A sighting device according to the invention, collaborative or active, is installed upstream of the assembly. This sighting system, which comprises an active target pattern MAM, presents to the subject the image of a luminous point, deviating periodically from the sought sighting axis. The patient is then invited to follow all the movements of this image. Each time that the image returns to the axis, and after an adjustable latency time, a series of interferometric measurements is carried out. The periodic movement of the viewing direction makes it possible to obtain from the patient an improved fixation capacity when he aims at the desired axis. The amplitude and the frequency are adaptable to the subject and to the measurements undertaken. For reasons of convenience, the target pattern may be produced with a simple office computer on which a light point is displayed and moved. The active target pattern MAM, the adaptive optics, the source S and the image shot are synchronized.

Figure 2A:
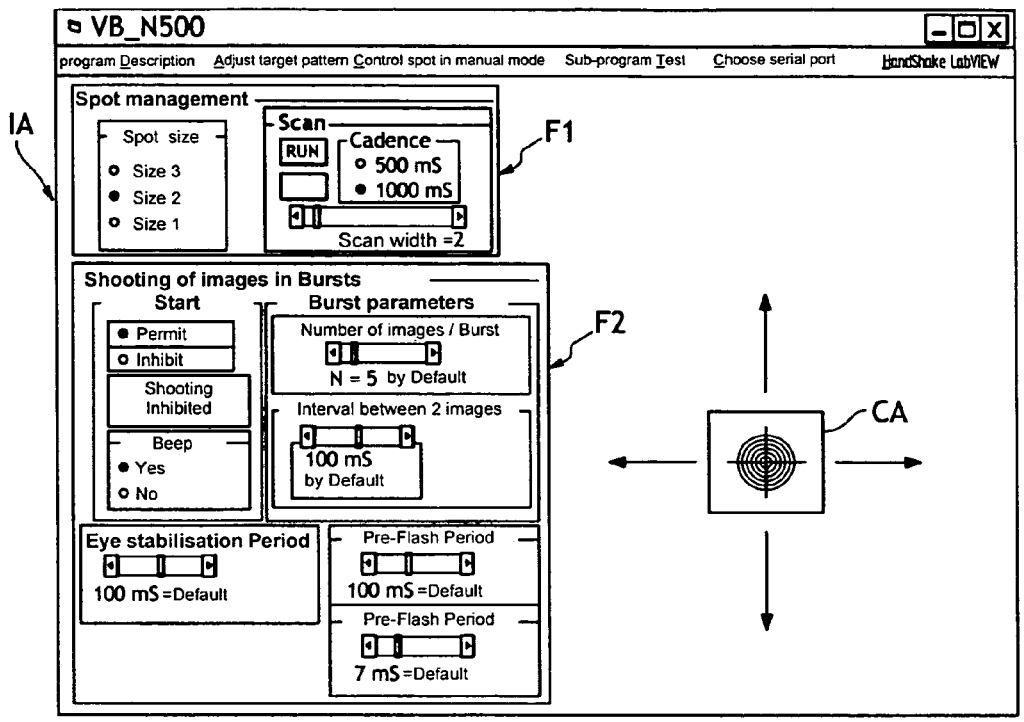
FIGS. 2A and 2B represent respectively a first and a second embodiment of active targets implemented in a sighting device according to the invention, on a computer screen.
Figure 2B:
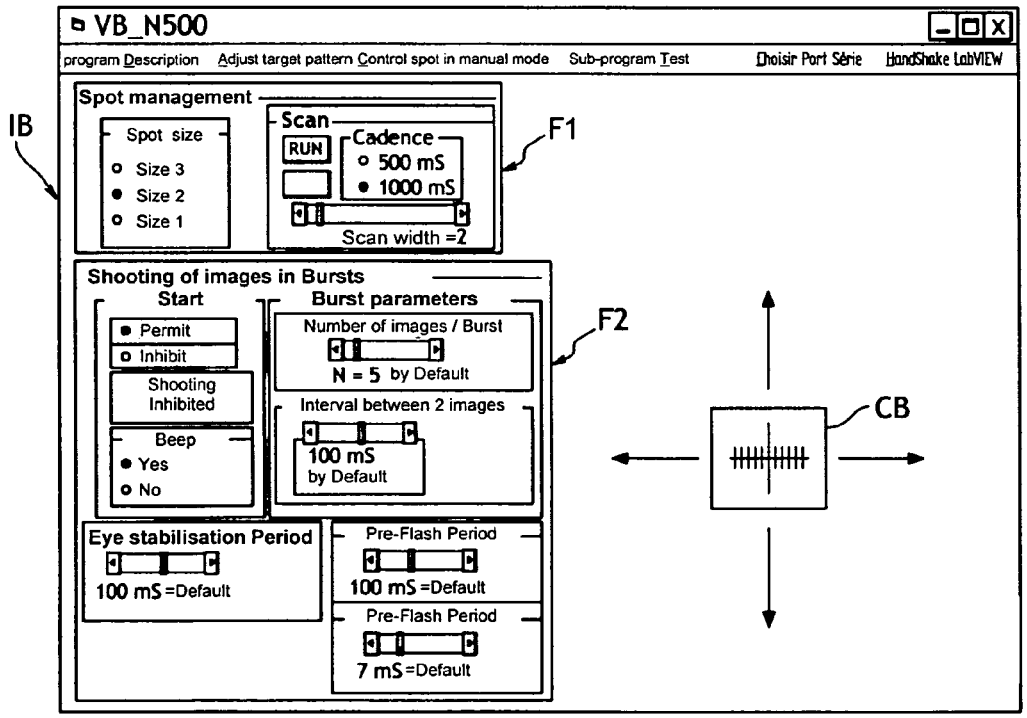

The active target pattern may be produced on the screen of a computer or a monitor connected to a control system (not shown) of the sighting device, as illustrated by FIGS. 2A and 2B. In this embodiment, a graphic user interface IA or IB comprises for example a first window F1 for managing a spot, a second window F2 for shooting an image in bursts, and a moving target CA or CB on a part of the screen. This moving target may be produced, for example, as a conventional representation target consisting of concentric circles and a sighting cross in the centre of these circles (FIG. 2A), or even as a graduated cursor and a superimposed sighting cross (FIG. 2B).

In the example illustrated in FIG. 3, the system is arranged so that the target of the active target pattern MAM is visible by both eyes OD1 and OG1 of the subject to be examined. A sighting with both eyes may actually improve the fixation or stability performances and facilitate the examination. In this example, the image of the target pattern is introduced into the optical path between the reference source SLD and the eye examined by a separator BST3.

This separator may be chosen dichroic for reflecting 50% of all the light coming from the target pattern MAM towards the examined eye OEX, and transmitting the remaining 50% towards the other eye OV1 or OV2 to enable a sighting by both eyes. The dichroic separator BST3 then transmits all the light from the reference source SLD towards the examined eye OEX, at the same time taking advantage of a spectral difference between the reference source SLD (830 nm) and the target pattern MAM (800 nm). A 50/50 separator plate, which is spectrally totally neutral is also suitable, but 50% of the light from the SLD is then sent towards the eye which is not studied. A filter makes it possible to eliminate this image if it is judged uncomfortable by the subject.

In order to be able to examine either eye, while simultaneously ensuring a sighting by both eyes, the system has a central examination location OEX, as well as two sighting locations OV1 and OV2, arranged on either side of this examination location OEX.

When the left eye is at the central location in order to be examined, the right eye receives the image of the target pattern MAM in its sighting location OV1 by the retractable return means, for example two mirrors MT1 and MT2. When it is the right eye which is at the location OEX, the return means may be retracted or cancelled and the image of the target pattern MAM reaches the left eye in its sighting location OV2.

As illustrated in FIG. 3, the system may also comprise, or collaborate with, means IRIS of tracking movements of the eye to be examined, collaborating with the tomography device. This may be, for example, a camera with image recognition carrying out a monitoring or "tracking", for example of the retina or of the pupil or edges of the iris, in order to detect and evaluate the movements of the eye.

Knowledge of the movements of the eye may then be used by the system to adapt to displacements of the zone to be examined, for example by coordinating the adjustments and exposures with the different positions detected or envisaged for this zone to be examined, or by enabling a spatial and/or temporal optimisation of the adaptive optics. It is possible, for example, to take advantage of natural periods of stabilisation of the pupil or the retina in order to carry out all or some of the desired adjustments or measurements.

The image of the eye examined reaches the means IRIS of tracking the eye by a separator BST2 inserted into the optical path, for example between the eye and the reference source SLD. Advantageously, for example in order not to discomfort the subject, this separator BST2 is dichroic and the tracking of the movements of the eye is carried out in non-visible light, for example, infrared.

The means of tracking IRIS may comprise, for example, a device for measuring ocular movements, such as those developed by the Metrovision company.

The invention may in particular be used to produce or complement a device for retinal imaging, or for corneal topography, or for measuring a film of tears.

Of course, the invention is not limited to the examples which have just been described and numerous adjustments can be made to these examples without exceeding the framework of the invention.

The invention claimed is:

1. A system for examining the eye by in vivo tomography, comprising a tomography device including:
    a Michelson interferometer, producing a full field optical coherence tomography OCT setup, adaptive optical means, arranged between the interferometer and an eye to be examined, producing a correction of the wavefronts originating from the eye as well as those reaching the eye,
    means for detection, arranged downstream of the interferometer, capable of carrying out, without synchronous modulation or detection, the interferometric measurement according to the OCT principle, and
    a sighting device comprising at least one moving target, having a programmable shape or a programmable trajectory, said target being displayed on viewing means and visible from at least one of the eyes of said patient during the examination period.

2. The system according to claim 1, wherein the sighting device and the tomography device collaborate by using an a priori knowledge of the trajectory or of the shape of the target to readjust the images of the eye as a function of said trajectory.

3. The system according to claim 1, further including means for tracking movements of the eye to be examined, collaborating with the tomography device.

4. The system according to claim 1, further including means for enabling the image of the target to reach both eyes of the subject to be examined.

5. They system according to claim 1, further including means for enabling the image of the target to reach the unexamined eye of the target selectively from one side or from the other side of the examined eye.

* * * * *